US00PP21871P2

(12) United States Plant Patent
Egger

(10) Patent No.: US PP21,871 P2
(45) Date of Patent: Apr. 12, 2011

(54) ***HEUCHERA* PLANT NAMED 'BERRY SMOOTHIE'**

(50) Latin Name: ***Heuchera* hybrid**
Varietal Denomination: Berry Smoothie

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 65 days.

(21) Appl. No.: 12/653,628

(22) Filed: Dec. 14, 2009

(51) Int. Cl.
*A01H 5/00* (2006.01)

(52) U.S. Cl. ..... Plt./440

(58) Field of Classification Search ..... Plt./440
See application file for complete search history.

*Primary Examiner* — Kent L Bell

(74) *Attorney, Agent, or Firm* — Klarquist Sparkman, LLP

(57) ABSTRACT

A new and distinct hybrid of *Heuchera* plant characterized by it salmon-rose spring leaves to rose-purple summer leaves, large leaves and habit, and excellent vigor.

2 Drawing Sheets

Botanical denomination: *Heuchera* hybrid.
Variety designation: 'Berry Smoothie'.

BACKGROUND OF THE INVENTION

The present invention relates to a new and distinct cultivar of *Heuchera* and given the cultivar name of 'Berry Smoothie'. *Heuchera* is in the family *Saxifragaceae*. *Heuchera* 'Berry Smoothie' originated from a cross between *Heuchera* 794-3, a proprietary non-commercial hybrid, as the seed parent, and *Heuchera* 788-2, a proprietary non-commercial hybrid, as, as the pollen parent. This was part of a planned breeding program to create the different foliage colors using *Heuchera villosa* in the breeding lines.

Compared to the seed parent, *Heuchera* 794-3, the new cultivar has brighter leaf color.

Compared to the pollen parent, *Heuchera* 788-2, the new cultivar has much larger leaves, taller flower stalks, and a bigger habit. The foliage color for the new cultivar is brighter.

Compared to *Heuchera* 'Beaujolais' (U.S. Plant Pat. No. 19,577) the new cultivar has a larger habit, shorter inflorescences, and leaves that are an intense rose color in the spring and a rose purple color in the summer rather than burgundy colored in the spring and dark in the summer. They both have the large round leaves along with the heat and humidity tolerance of the *Heuchera villosa* group.

This new *Heuchera* is uniquely distinguished by its very large salmon-rose spring leaves to rose-purple summer leaves. In addition it has a large mounding habit, excellent vigor, and excellent tolerance to heat and humidity.

This new cultivar has been reproduced only by asexual propagation (tip cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows the intense spring foliage color of *Heuchera* 'Berry Smoothie'.

FIG. 2 shows the new cultivar in bloom in the fall in Canby, Oreg.

DETAILED PLANT DESCRIPTION

Figure 3:
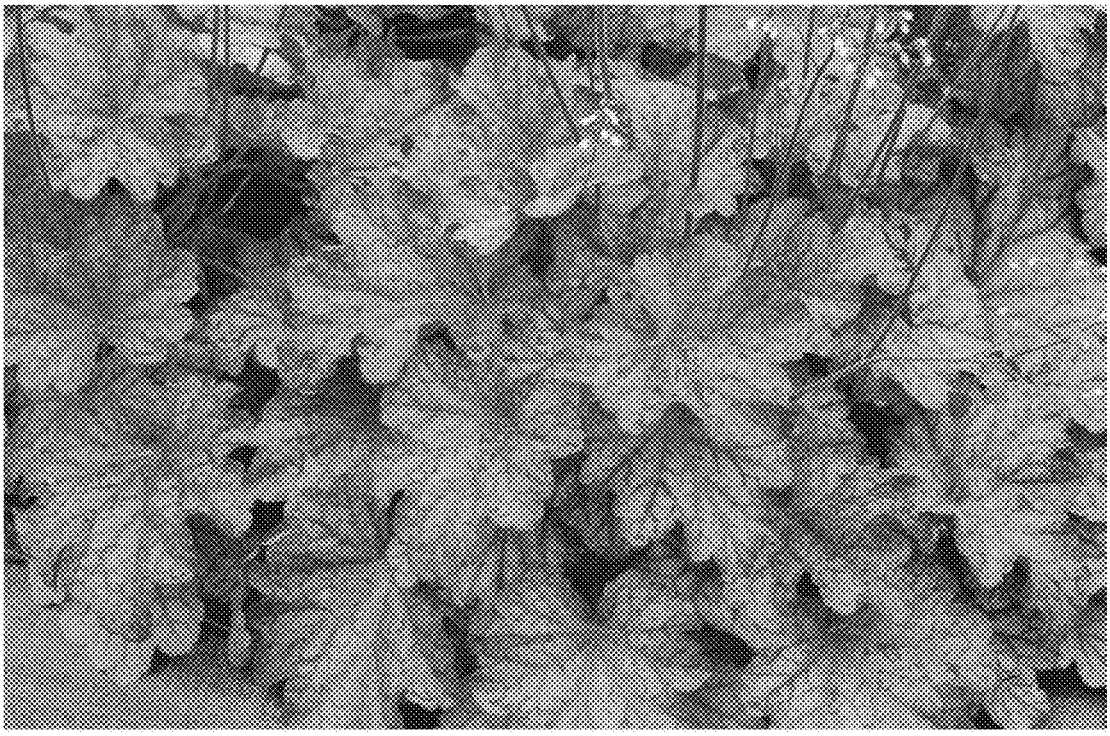
FIG. 3 shows the summer foliage color.

The following is a detailed description of the new *Heuchera* cultivar based on observations taken in mid July of a nine-month-old specimen growing in the ground in the trial bed under high shade and with added irrigation in the summer months in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The Royal Horticultural Society Colour Chart, 1999 edition.

Plant:

*Form.*—Basal rosette, herbaceous perennial.
*Hardiness.*—USDA Zone 4 to 9.
*Size.*—21 cm tall from top of the foliage to the ground and 55 cm wide.
*Habit.*—Mounding.
*Vigor.*—Excellent.
*Roots.*—Fibrous, freely branching, fine, and white in color; roots develop easily from tip cuttings.

Leaf:

*Type.*—Simple.
*Arrangement.*—Rosette.
*Shape.*—Broadly ovate.
*Lobing/division.*—7 shallow lobes, the terminal is the longest; shallow secondary lobes.
*Venation.*—Palmate.
*Margins.*—Broadly crenate and somewhat undulate.
*Apex.*—Mucronulate.
*Base.*—Cordate, lobes not overlapping at the base.
*Blade size.*—Grows to 17 cm long and 16 cm wide.
*Surface texture.*—Glandular on both sides.
*Petiole description.*—Grows to 17 cm long and 4 mm wide, glandular hairs, Greyed Purple 187B.
*Leaf color.*—Topside, spring leaves have a base color of Greyed Purple 185A with a heavy silver veil of between Greyed Purple 185D and Grey 201D, bottom side Greyed. Purple 185A; summer leaves have a base color of Greyed Orange 166A with a heavy silver pink veil between Grey 201 D and Greyed Purple 186A; bottom side, Greyed Purple 187B; winter color top side dull purple, Greyed Purple 187A, with a silver veil, Grey 201B, bottom side, Greyed Purple 187B.

Inflorescence:

*Size.*—Grows to 8 cm wide and 20 cm long.

*Type.*—Thyrse.

*Number of flowers per thyrse.*—About 100.

*Number of thyrse.*—15.

*Peduncle.*—grows to 55 cm tall, 5 mm wide at base, Greyed Purple 187A, glandular hairs, with 0 to 1 petiolate cauline leaves (blades ovate to orbicular, grows to 3 cm long and 3.5 cm wide with an incised margin, Greyed Purple 187A with veins Black 202A).

*Pedicel.*—Variable in size, with glandular hairs, Greyed Purple 187A.

*Bloom period.*—Late June through July in Canby, Oreg.

Flower bud:

*Size.*—2.5 mm wide and 4 mm long.

*Description.*—Glandular puberulent, ovoid.

*Color.*—Greyed Purple 186C on bottom half with areas of White 155D on top half.

Flower:

*Type.*—Perfect.

*Shape.*—Campanulate.

*Size.*—5 mm long and 4 mm wide.

*Corolla description.*—5 lobed, 3 mm long and 1 mm wide, spatulate, tip acute, margin entire, glabrous on top side and glandular on bottom side, White 155D on both sides.

*Calyx description.*—Campanulate, 5 mm long and 4 mm wide, with 5 lobes divided ⅔ way to the base, each 1.5 mm wide and 2 mm long, glandular hairs outside and glabrous inside, tips obtuse, margin entire; bicolor light pink/dark pink flower color, outside Greyed Purple 185C on tube and on lobe tips, Red 36D on lobes; inside White 155A.

*Stamen description.*—5 in number, filaments 2 mm long, White 155D, anthers sterile, 0.3 mm, Orange 25C.

*Pistil description.*—1, 2-beaked, 5 mm long; ovary 2 mm long, Red 36D; style 3 mm long, White 155A, stigma White 155A.

*Fragrance.*—None.

*Lastingness.*—Each thyrse blooms for about 2 weeks on the plant.

Fruit:

*Type.*—Two beaked capsule.

*Size.*—7 mm deep by 3 mm wide.

*Fertility.*—Good.

*Color.*—Brown 200D.

Seed:

*Shape.*—Linear.

*Size.*—1 mm long.

*Color.*—Black 202A.

Pest and disease tolerance: Excellent disease resistance to powdery mildew, the common problem of *Heuchera*. Susceptible to *Heuchera* rust and root weevils.

COMPARISON TO SIMILAR HEUCHERA

Compared to *Heuchera* 'Beaujolais' (U.S. Plant Pat. No. 19,577) the new cultivar has a larger habit, shorter inflorescences, and leaves that are more richly rose purple in color.

I claim:

1. A new and distinct *Heuchera* plant as herein illustrated and described.

* * * * *

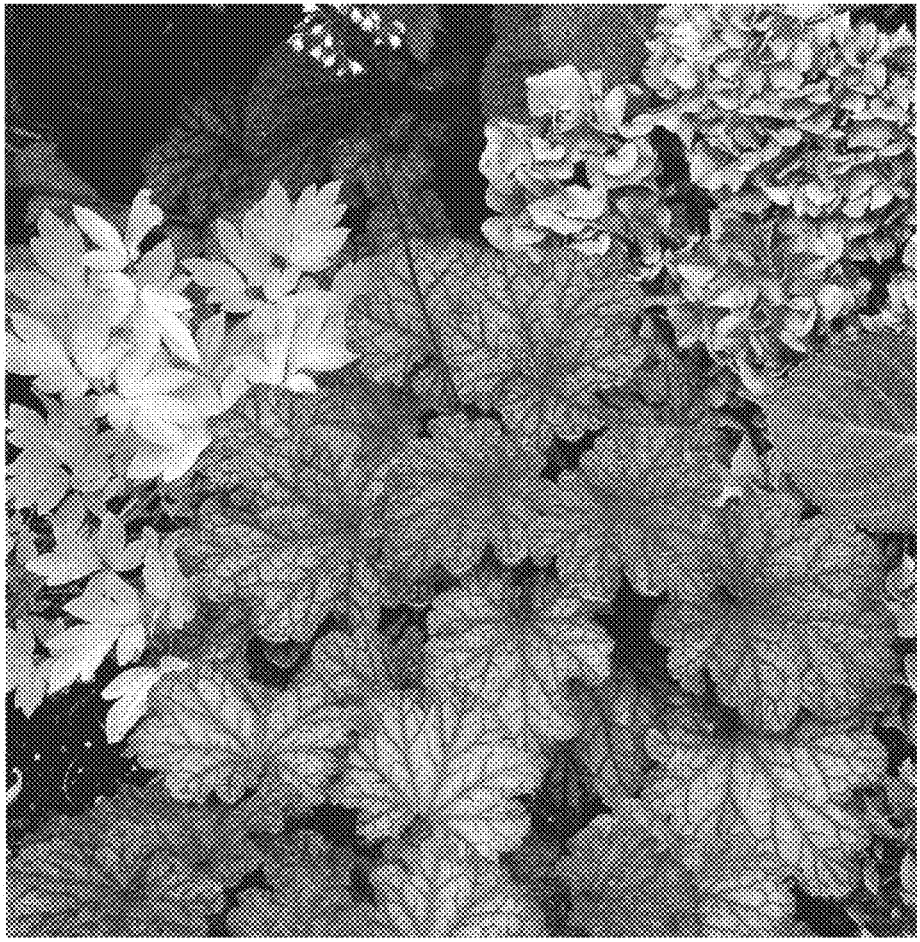

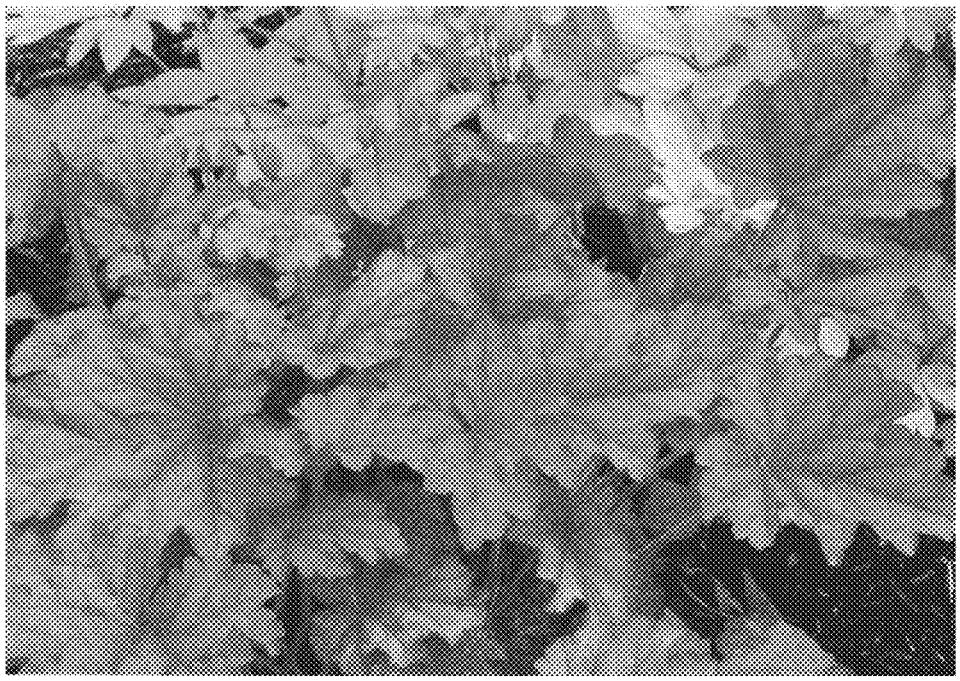
Figure 1 above, Figure 2 below.